United States Patent [19]
Lafontaine et al.

[11] Patent Number: 5,647,847
[45] Date of Patent: Jul. 15, 1997

[54] BALLOON CATHETER WITH IMPROVED PRESSURE SOURCE

[75] Inventors: Daniel M. Lafontaine, Plymouth; Daniel O. Adams, Orono; John W. Humphrey, Eden Prairie, all of Minn.

[73] Assignee: SCIMED Life Systems, Inc., Maple Grove, Minn.

[21] Appl. No.: 334,831

[22] Filed: Nov. 4, 1994

Related U.S. Application Data

[63] Continuation-in-part of Ser. No. 308,025, Sep. 16, 1994, Pat. No. 5,545,133.

[51] Int. Cl.$^6$ .................................................. A61M 29/00
[52] U.S. Cl. ............................................. 604/96; 604/97
[58] Field of Search ......................... 604/96, 97, 121, 604/118, 65–67, 98, 99, 100; 128/673, 774, 775, 778, 748

[56] References Cited

U.S. PATENT DOCUMENTS

| | | |
|---|---|---|
| 3,190,291 | 6/1965 | Foley . |
| 3,378,011 | 4/1968 | Vitello . |
| 3,379,197 | 4/1968 | Hayes . |
| 3,602,226 | 8/1971 | Ericson . |
| 3,675,658 | 7/1972 | Taylor . |
| 3,818,903 | 6/1974 | Bleecker . |
| 4,227,534 | 10/1980 | La Rosa . |
| 4,244,366 | 1/1981 | Raines . |
| 4,245,639 | 1/1981 | La Rosa . |

(List continued on next page.)

FOREIGN PATENT DOCUMENTS 2209121  5/1989  United Kingdom .

OTHER PUBLICATIONS

*Therapy and Prevention Congenital Heart Disease*, AHA Circulation brochure, "Anigioplasty for coarctation of the aorta: long–term results", R. Cooper et al.; vol. 75, No. 3, pp. 600–604, Mar. 987.

*European Heart Journal*, "Anterograde percutaneous transseptal valvuloplasty in a case of severe calcific aortic stenosis", vol. 8, pp. 190–193, Feb. 1987.

*Clinical Cardiology*, "Balloon Aortic Valvuloplasty in Children", vol. 13, pp. 458–466, Jul. 1990.

"Balloon Catheters and Transluminal Dilataion: Technical Considerations," John Abele, *American Journal of Roentgenology*, vol. 135, pp. 901–906, Nov. 1980.

(List continued on next page.)

*Primary Examiner*—John D. Yasko
*Attorney, Agent, or Firm*—Robert E. Atkinson

[57] ABSTRACT

A balloon catheter which has an elongate shaft with an inflatable balloon connected to its distal end and a manifold connected to its proximal end. The manifold may be fixedly or removably attached to the shaft and includes a barrel with a plunger movably disposed inside it. The manifold may be held with one hand and the plunger may be actuated with one finger or thumb on the same hand. The barrel may have an internal volume of less than 5 cc and an internal diameter of less than 0.25 inches. The catheter also has a prep port which may be connected at or near the proximal end of the catheter. The prep port facilitates prepping of the catheter system. A seal (e.g. a releasable cap or a valve) may be connected to the prep port for sealing off the prep port during use. A pressure transducer may be mounted to the catheter (e.g. on the shaft, the manifold, the prep port, or the seal) to permit measurement of the pressure within the inflation lumen and the balloon. The pressure transducer may be operably connected to a pressure display and the display may be connected to the proximal end of the catheter or may be remotely located from the catheter. Data may be transmitted to the remote display by wire or wireless transmission (e.g. infrared, radio frequency, or magnetic transmission). Alternate embodiments and methods of use are also disclosed.

42 Claims, 11 Drawing Sheets

U.S. PATENT DOCUMENTS

| | | |
|---|---|---|
| 4,332,254 | 6/1982 | Lundquist . |
| 4,370,982 | 2/1983 | Reilly . |
| 4,413,982 | 11/1983 | Schjeldahl et al. . |
| 4,429,724 | 2/1984 | Dorros et al. . |
| 4,439,185 | 3/1984 | Lundquist . |
| 4,446,867 | 5/1984 | Leveen et al. . |
| 4,476,866 | 10/1984 | Chin . |
| 4,535,757 | 8/1985 | Webster, Jr. . |
| 4,592,364 | 6/1986 | Pinto . |
| 4,651,738 | 3/1987 | Demer et al. . |
| 4,655,749 | 4/1987 | Fischione . |
| 4,740,203 | 4/1988 | Hoskins et al. . |
| 4,758,223 | 7/1988 | Rydell . |
| 4,781,192 | 11/1988 | Demer . |
| 4,838,864 | 6/1989 | Peterson . |
| 4,878,903 | 11/1989 | Mueller . |
| 4,929,238 | 5/1990 | Baum . |
| 4,930,341 | 6/1990 | Euteneuer . |
| 4,944,726 | 7/1990 | Hilal et al. . |
| 4,954,239 | 9/1990 | Mueller . |
| 5,004,472 | 4/1991 | Wallace . |
| 5,009,662 | 4/1991 | Wallace et al. . |
| 5,019,041 | 5/1991 | Robinson et al. . |
| 5,021,046 | 6/1991 | Wallace . |
| 5,113,868 | 5/1992 | Wise et al. . |
| 5,152,776 | 10/1992 | Pinchuk . |
| 5,156,598 | 10/1992 | Skakoon et al. . |
| 5,171,299 | 12/1992 | Heitzmann et al. . |
| 5,196,017 | 3/1993 | Silva et al. . |
| 5,209,728 | 5/1993 | Kraus et al. . |
| 5,215,523 | 6/1993 | Williams et al. . |
| 5,265,593 | 11/1993 | Odland . |
| 5,273,537 | 12/1993 | Haskvitz et al. . |
| 5,275,169 | 1/1994 | Afromowitz et al. . |
| 5,284,480 | 2/1994 | Porter et al. . |
| 5,318,533 | 6/1994 | Adams et al. . |
| 5,338,301 | 8/1994 | Diaz . |

OTHER PUBLICATIONS

"Angiographic Patterns of Balloon Inflation During Percutaneous Transliminal Coronary Angioplasty: Role of Pressure–Diameter Curves in Studying Distensibility and Elasticity of the Stenotic Lesion and the Mechanism of Dilation," Hjemdahl–Monsen et al., *Journal of the American College of Cardiology*, vol. 16, No. 3, pp. 569–575, Sep. 1990.

"High Intensity Ultrasound Increase Distensibility of Calcific Atherosclerotic Arteries," Demer et al., *Journal of the American College of Cardiology*, vol. 18, No. 5, pp. 1259–1962, Nov. 1991.

BALLOON CATHETER WITH IMPROVED PRESSURE SOURCE

CROSS-REFERENCE TO RELATED APPLICATIONS

This case is a continuation-in-part of commonly assigned U.S. patent application Ser. No. 08/308,025 filed Sep. 16, 1994 now U.S. Pat. No. 5,545,133, the entire disclosure of which is incorporated herein by reference.

FIELD OF THE INVENTION

The present invention generally relates to balloon catheters. More specifically, the present invention relates to balloon dilation catheters used for the treatment of vascular disease. Those skilled in the art will recognize the benefits of applying the present invention to similar fields not discussed herein.

BACKGROUND OF THE INVENTION

A wide variety of therapeutic techniques have been developed to correct or inhibit vascular diseases. Coronary artery disease (CAD), for example, is an adverse condition of the heart in which the blood flow to the heart muscle is partially or totally restricted by occlusive material in the coronary arteries which narrows the blood flow lumen. The occlusive materials deprive portions of the heart muscle of essential oxygenated blood.

CAD may be treated by a surgical technique referred to as coronary artery bypass graft (CABG) surgery. This surgical procedure involves supplementing blood flow to the heart muscle by grafting a non-native conduit such as a saphenous vein graft (SVG) to the heart. A first end of the SVG is connected to the ascending aorta (proximal to the occlusive material) and the other end is connected to the artery distal of the occlusive material. Although this technique has been useful for treating CAD in native coronary arteries, it is not uncommon for occlusive material to form over time in the SVG thereby necessitating additional therapy.

Percutaneous translumenal coronary angioplasty (PTCA) has gained wide acceptance as an effective and less invasive alternative to CABG surgery in certain patient groups. The PTCA procedure involves the use of an angioplasty balloon catheter, several types of which are well known in the art. The balloon catheter is inserted into the body via the femoral artery and navigated to the coronary arteries assisted by a guide catheter and (usually) a guide wire. The balloon is positioned across the restriction in the artery and subsequently inflated. The inflated balloon widens the restriction and restores blood flow to portions of the heart muscle previously deprived of oxygenated blood.

A PTCA balloon catheter typically has a manifold at its proximal end and a balloon at its distal end. The manifold facilitates connection to an inflation device which is used to inflate and deflate the balloon. An example of a conventional inflation device is disclosed in U.S. Pat. No. 5,019,041 to Robinson et al. which also includes a good discussion of related prior art inflation devices.

Prior art inflation devices are usually in the form of a modified 10 cc or 20 cc syringe. For example, the Classic™ inflation device (available from SCIMED Life Systems, Inc. located in Minnesota) includes a modified 20 cc syringe housed with an illuminated pressure gauge, threaded plunger and lock mechanism. This inflation device measures about 9×2×2 inches and weighs about 189 grams which renders it relatively bulky as compared to a conventional PTCA balloon catheter which measures about 0.039 inches diameter× 57 inches length and weighs about 4 grams. Due to its size and weight, a typical inflation device may interfere with the physician's ability to delicately manipulate a balloon catheter through the vascular system. As a result, current day inflation devices incorporate a long flexible line as a part of the inflation device for connection to the catheter. Although the physician may choose to disconnect the inflation device from the balloon catheter while manipulating it, such additional steps are inconvenient, increase the time required for the procedure, increase the probability of introducing air into the system, and increase the probability that the vascular position of the balloon will be accidentally displaced when attempting to reconnect the inflation device. As such, it is desirable to minimize the size and weight of an inflation device to avoid these problems.

Due to their relatively large size, prior art catheter systems usually require two operators, namely one person to maintain catheter position and another person to operate the inflation device. Although the catheter position may be maintained by locking the guide catheter hemostatic seal (usually a Y-adapter) onto the catheter shaft, such a step is dependent on maintaining guide catheter position and is therefore not as reliable as maintaining position by manually gripping the catheter. Also, manually maintaining the catheter position allows the treating physician to easily make quick and accurate adjustments in balloon position between inflations.

An inflation device is preferably capable of inflating to pressures of at least 300 psi, and is preferably capable of drawing a near perfect vacuum (perfect vacuum=−14.7 psi at sea level). Prior art inflation devices commonly use a large bore (e.g. 20 cc) syringe to obtain a higher vacuum. In order to reach and maintain high inflation pressure, a relatively high force is required to actuate and hold a large bore inflation device. To overcome this problem, some prior art devices have utilized a threaded plunger and lock mechanism, an example of which is disclosed in Robinson '041. With a threaded plunger, a high longitudinal force and resulting high pressure may be generated by rotating the plunger with moderate actuation torque. The threaded plunger may be engaged by a lock mechanism to maintain the position of the plunger and thus maintain high pressures for a duration of time. Although such a feature reduces the necessary actuation force, it only adds to the size, weight and complexity of the inflation device and thus fails to overcome the corresponding disadvantages described previously.

Other prior art inflation devices utilize a small bore syringe (e.g. 1–2 cc) in combination with a large bore syringe (e.g. 10–20 cc) to generate high inflation pressures with relatively low actuation force. The small bore syringe takes advantage of the principal that force is equal to pressure multiplied by area (F=P×A) where the area of the small bore syringe is sufficiently small to reduce the force required to generate high pressure. Examples of such inflation devices are disclosed in U.S. Pat. Nos. 4,476,866 to Chin, 4,740,203 to Hoskins et. al., and 4,758,223 to Rydell. However, these inflation devices do not allow the small bore syringe to be used without the large bore syringe. As such, the combination of large and small bore syringes does not subtract but rather adds to the weight of the inflation device. Again, while these inflation devices reduce the actuation force required to generate high pressures, they do not overcome the problems associated with size and weight as identified previously.

In addition to the disadvantages associated with size and weight, prior art inflation devices have relatively high internal compliance. Compliance refers to the increase or decrease in volume of the fluid path (i.e. the inside of the inflation device and the inflation lumen of the catheter) in response to changes in pressure, in addition to the compressibility of the inflation fluid and any air trapped in the fluid path. High internal compliance is not desirable because it decreases the responsiveness of the system and increases the dampening effect on dynamic balloon response. High internal compliance also increases the tendency of the balloon to continue to expand after the lesion yields, thus increasing the probability of dissection. Furthermore, high internal compliance decreases balloon deflation rate which compromises the physicians ability to relieve ischemia and other adverse reactions to prolonged balloon inflation. Thus, it is desirable to reduce the internal compliance to overcome these disadvantages. Compliance may be reduced by providing a more rigid structure defining the fluid path and by decreasing the volume of inflation fluid and any air trapped in the fluid path. The volume of inflation fluid may be reduced by decreasing the volume of the fluid path, namely the inside of the inflation device and the inflation lumen of the balloon catheter.

In summary, there is a need for a catheter and inflation device system which minimizes size and weight, which is operable by a single person, which minimizes actuation force, and which minimizes internal compliance.

SUMMARY OF THE INVENTION

The present invention overcomes the disadvantages of the prior art as discussed above and offers other advantages as well. One embodiment of the present invention is a balloon catheter which has an elongate shaft with an inflatable balloon connected to its distal end and a manifold connected to its proximal end. The manifold may be fixedly or removably attached to the shaft. The manifold includes a barrel with a plunger movably disposed inside which displaces inflation fluid into the balloon by way of an inflation lumen inside the shaft. The manifold may be held with one hand and the plunger may be actuated with one finger or thumb on the same hand. The catheter also has a prep port which may be connected at or near the proximal end of the catheter. The prep port is releasably connectable to a fluid source so that inflation fluid can be introduced into the barrel and inflation lumen. The barrel may have an internal volume of less than 5 cc and an internal diameter of less than 0.25 inches. A seal may be connected to the prep port for sealing the inflation lumen when the fluid source is not connected to the prep port. The seal may be a releasable cap or a valve, for example. A pressure transducer may be mounted to the catheter (e.g. on the shaft, the manifold, the prep port, or the seal) to permit measurement of the pressure within the inflation lumen and the balloon. The pressure transducer may be operably connected to a pressure display and the display may be connected to the proximal end of the catheter or may be remotely located from the catheter. Data may be transmitted to the remote display by wire or wireless transmission (e.g. infrared, radio frequency, or magnetic transmission).

Another embodiment of the present invention is a balloon catheter system including a balloon catheter, an inflation device, and a fluid source. The balloon catheter includes an elongate shaft with an inflatable balloon connected to its distal end and a manifold connected to its proximal end. The manifold includes an inflation port which is in fluid communication with the inflation lumen. The inflation device includes a barrel which is in fluid communication with the inflation lumen and a plunger movably disposed in the barrel. The inflation device may be held with one hand and the plunger may be actuated with one finger or thumb on the same hand. A prep port is connected to the inflation device and is in fluid communication with the inflation lumen of the catheter when connected thereto. The inflation device is fixedly or removably attached to the catheter by way of a connection port on the inflation device which connects to the manifold of the catheter. The barrel may have an internal volume less than 5 cc and an internal diameter of less than 0.25 inches. A seal may be connected to the prep port for sealing the inflation device during balloon inflation. The seal may be a releasable cap or a valve, for example. A pressure transducer may be mounted on the catheter to permit measurement of the pressure within the inflation lumen and the balloon. The pressure transducer may be operably connected to a pressure display which may be connected to the catheter or remotely located from the catheter. The pressure transducer may be fluidic (e.g. bourdon gauge), mechanical (e.g. spring gauge) or electronic. The pressure display may be analog or digital (or both) and is preferably an electronic analog display. A lock mechanism or a pair of lock mechanisms may be used to maintain the position of the plunger relative to the barrel. The lock mechanism may include a spring biased release button. The lock mechanism preferably employs threads for rotational actuation but may also employ other lock mechanisms such as a collet and compression collar.

Yet another embodiment of the present invention is a balloon catheter which has an elongate shaft with an inflatable balloon connected to its distal end and a display fixedly connected to the catheter at or near the proximal end. The display may be fluidic or electronic, and the electronic display may be analog, digital, or a combination of both.

In practice, a method of using a balloon catheter (wherein the catheter includes an elongate shaft having a proximal end, a distal end and an inflation lumen extending therethrough; an inflatable balloon connected to the distal end of the shaft and in fluid communication with the inflation lumen; a manifold connected to the proximal end of the shaft, the manifold having a barrel containing a plunger movably disposed therein, the barrel in fluid communication with the inflation lumen; and a prep port connected to the proximal end of the catheter and in fluid communication with the inflation lumen) includes the steps of (1) connecting a fluid source to the prep port; (2) displacing gas in the barrel and inflation lumen with the fluid from the fluid source; (3) disconnecting the fluid source from the prep port; (4) fluidly closing the prep port; and (5) inflating the balloon by displacing the plunger distally. The plunger may be released after inflation to detect elastic recoil of the lesion. Deflation of the balloon may be accomplished by displacing the plunger proximally. The steps of inflating and deflating may be done in rapid succession at various frequencies including sonic frequencies. The displacement of the plunger may be measured during inflation to determine the volume of the lesion. In addition, the force required to displace the plunger may be compared (e.g. by plotting a graph) to the distance the plunger is displaced in order to determine a physical characteristic of the lesion.

The advantages of the present invention can be fully appreciated with a thorough review of the entire specification and drawings. Those skilled in the art will appreciate other advantages not fully described herein. Furthermore, while the disclosure focuses on balloon dilation catheters, those skilled in the art will recognize that the invention may be incorporated into other devices and methods of use without departing from the spirit of the invention.

BRIEF DESCRIPTION OF THE DRAWINGS

FIGS. 1–4 show various manifold designs which are interchangeable consistent with the corresponding teachings for each figure.

FIG. 10 shows the balloon response to a single inflation and deflation. FIG. 11 shows the balloon response to cyclic inflation and deflation. FIG. 12 shows the response of a synthetic vascular lesion to balloon dilation.

DETAILED DESCRIPTION OF THE INVENTION

The following detailed description should be read with reference to the drawings in which like elements in different figures are numbered identically. The drawings, which are not necessarily to scale, depict selected embodiments and are not intended to limit the scope of the invention.

Examples of constructions, materials, dimensions and manufacturing processes are provided for selected elements. All other elements employ that which is known to those skilled in the field of the invention. Those skilled in the art will recognize that many of the examples provided have suitable alternatives which may also be utilized.

The catheter system of the present invention may take the form of any balloon catheter used in a variety of medical procedures. For example, the catheter may take the form of a single-operator-exchange (SOE), fixed-wire (FW) or over-the-wire (OTW) type balloon catheter and may be used in coronary, peripheral, cerebral, and other vascular procedures, in addition to urethral and other non-vascular procedures. Other features such as perfusion and drug delivery may also be incorporated into the catheter system. For the purpose of the following discussion, the exemplary embodiments are directed to a catheter system which is particularly suitable for PTCA procedures. However, with simple modifications in construction, the catheter system of the present invention may be used for other medical applications not fully discussed herein.

Figure 1:
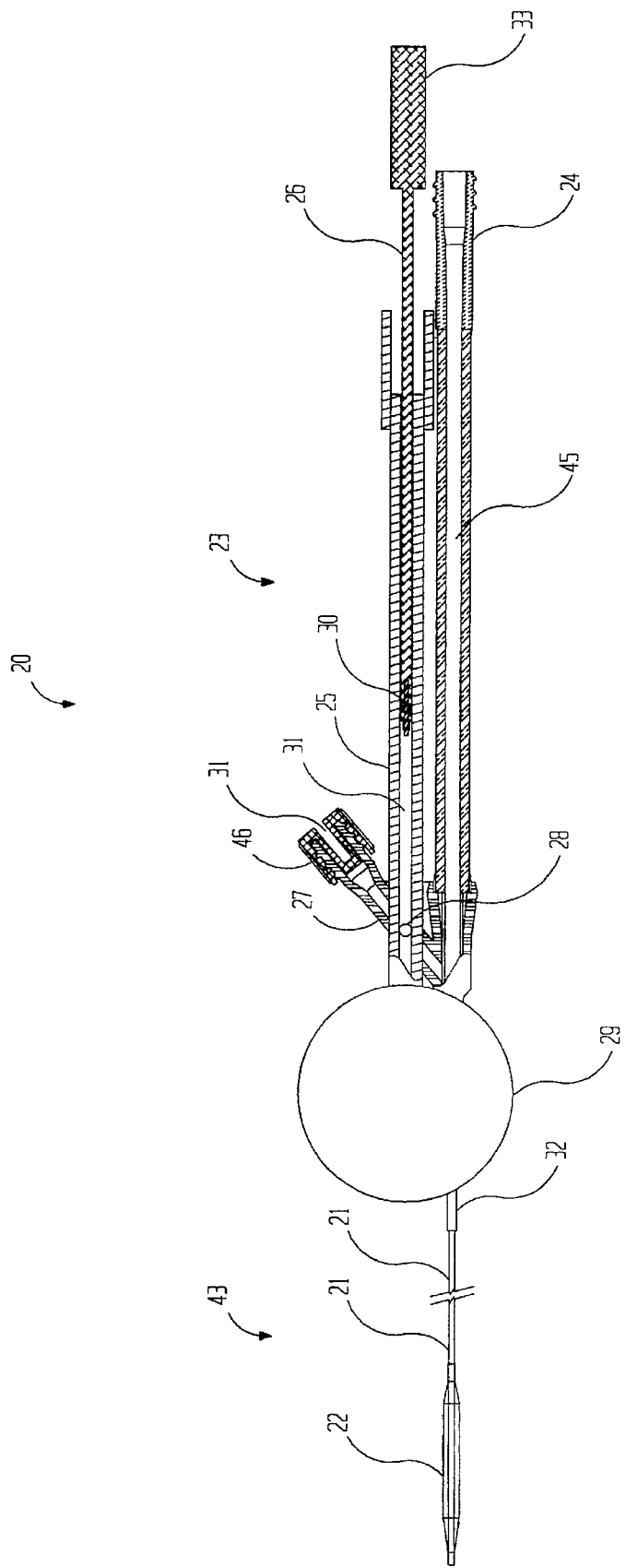
FIGS. 1, 3 and 4 are a partially sectioned views of various over-the-wire type catheter systems.

Refer now to FIG. 1 which shows an OTW balloon catheter system 20. Balloon catheter system 20 includes an OTW type balloon catheter 43 with a manifold 23 connected to its proximal end. The OTW type balloon catheter 43 may take on several forms which are known in the art. As shown, the OTW balloon catheter 43 includes an elongate shaft 21 with a balloon 22 connected to its distal end. The proximal end of the elongate shaft 21 is connected to the manifold 23 by conventional means and utilizes a strain relief 32 to reduce the potential for kinking therebetween. It is contemplated that the manifold 23 may be made of conventional materials such as polycarbonate and may be made by conventional means such as injection molding.

Because of the relatively small size of manifold 23, the catheter system 20 is operable by a single person whereas prior art catheter systems usually require two operators, namely one person to maintain catheter position and another person to operate the inflation device. Although the catheter 43 position may be maintained by locking the guide catheter hemostatic seal (usually a Y-adapter) onto the catheter shaft 21, such a step is dependent on maintaining guide catheter position and is therefore not as reliable as maintaining position by manually gripping the catheter 43. Also, manually maintaining the catheter 43 position allows the treating physician to easily make quick and accurate adjustments in balloon position between inflations. In addition to the single operator advantage, the small size of the manifold 23 may significantly reduce manufacturing costs, reduce packaging requirements, reduce storage space requirements, and reduce medical waste.

The manifold 23 includes a guide wire port 24 defining a guide wire lumen 45 therethrough which communicates with the guide wire lumen 45 inside the catheter 43. The guide wire port 24 allows a conventional guide wire (not shown) to be introduced into the catheter 43. The guide wire port 24 may be relatively long (as drawn) for handling purposes or it may be relatively short for manufacturing purposes. Manifold 23 also includes a barrel 25 with a plunger 26 movably disposed therein. The barrel 25 may be straight or curved and the plunger 26 may be flexible to slidingly fit into a curved barrel. The plunger 26 includes a plunger seal 30 at its distal end and a handle 33 at its proximal end. The inside of the barrel 25 is in fluid communication with the inflation lumen 31 such that when the plunger 26 is longitudinally displaced, inflation fluid is displaced into or out of the inside of the barrel 25, through the inflation lumen 31 inside the catheter 43, and into or out of the balloon 22. For purposes of the following discussion, the inside of the barrel 25 is labeled 31 to denote that it is in fluid communication with the inflation lumen 31 of the catheter 43. The inside of the barrel 25 has access to the inflation lumen 31 of the catheter 43 by way of fluid channel 28. The construction of plunger 26, plunger seal 30, and barrel 25 are discussed in more detail with reference to FIG. 5.

Manifold 23 is shown fixedly attached to the catheter 43 but may be releasably attached with simple modifications. In particular, the manifold 23 may incorporate a luer connection at its distal end which would be releasably connectable to a mating luer fitting on an inflation port of a conventional balloon catheter. Such a releasable manifold would not require a guide wire port (e.g., see manifold 41 in FIG. 2).

Manifold 23 further includes a prep port 27 in the form of, for example, a standard female luer fitting, which may have a cap 46 releasably secured thereto. Prep port 27 allows inflation fluid to be introduced into the inflation lumen 31 and the inside of the barrel 25 prior to in-vivo use. The cap 46 is secured to the prep port 27 after the gas in the inflation lumen 31 has been displaced with fluid (e.g. radiopaque contrast liquid solution) by way of a fluid source (not shown) such as a standard 20 cc syringe filled with liquid contrast solution. The cap 46 serves to seal the prep port 27 so that fluid does not escape from the inflation lumen 31 during inflation and deflation of the balloon 22. As such, the cap 46 may be replaced with a similarly functioning element such as a stop-cock valve or any other sealing means which does not significantly add to the size and weight of the catheter system 20. Such a seal may be manually operated or may be self sealing by utilizing an elastomer seal or a spring biased seal. It should also be noted that the prep port 27 may be located on the proximal end of the catheter shaft 21, on the manifold 23 (shown), on the handle 33, or on any other portion of the catheter system 20 which has access to the inflation lumen 31 and does not interfere with in-vivo use. If the prep port 27 were located on the handle 33 of the plunger 26, it is contemplated that access to the inflation lumen 31 could be provided by way of a lumen (not shown) extending through the handle 33, the plunger shaft 26 and the plunger seal 30. If the prep port were located on the catheter shaft 21, it is contemplated that access to the inflation lumen 31 could be provided by way of a flexible tube (not shown) with one end sealably connected to the shaft 21 adjacent the strain relief 32 and with the other end sealably connected to a conventional female luer fitting (not shown).

Manifold 23 also includes a generic pressure gauge 29 mounted thereon which is in fluid communication with the inflation lumen 31. The generic pressure gauge 29 may include a transducer, an electric circuit if necessary, and a display. Generic pressure gauge 29 may be a fluidic gauge (e.g. bourdon pressure gauge), a mechanical gauge (e.g. a spring gauge), or an electronic gauge (e.g. a digital gauge, an analog gauge, or both). An electronic analog pressure gauge is particularly suitable for use with the present invention and is discussed in more detail with reference to FIG. 9.

It is preferable that the generic pressure gauge 29 be fixedly attached to a proximal portion of the catheter system 20 so that the system 20 is completely self-contained. For example, the pressure gauge 29 may be connected to any part of the catheter system 20 which remains outside the body during use. However, it is contemplated that the pressure gauge 29 may be remotely located (i.e. away from the catheter system 20) but within monitoring range of the treating physician. This may be accomplished by providing an electrical connector (not shown) mounted on the proximal end of the catheter system 20 with one set of electrical leads (not shown) connected to a pressure transducer in fluid communication with the inflation lumen 31, and another set of electrical leads connected to a remote electronic circuit and display. Alternatively, the remote display may receive signals from the pressure transducer by way of an infrared transmitter, a radio transmitter, or a magnetic field transmitter. Examples of remote displays are disclosed in U.S. Pat. Nos. 5,318,533 to Adams et. al. and 5,021,046 to Wallace.

It is also contemplated that a other pertinent information may be displayed along with the pressure as discussed above. For example, it may be desirable to display procedure time, balloon diameter, balloon volume, vascular blood flow rate, and/or vascular pressure. Examples of devices utilizing such measuring and displaying means are disclosed in U.S. Pat. No. 5,318,533 to Adams et. al., U.S. Pat. No. 5,346,508 to Hastings, commonly assigned U.S. patent application Ser. No. 08/141,134 entitled Pressure Sensor, and commonly assigned U.S. patent application Ser. No. 08/142,498 entitled Balloon Inflation Measurement Apparatus.

Although means for measuring and remotely displaying such parameters are known in the art, incorporating a display fixedly attached to the catheter system 20 is believed to be novel. Such a feature would allow the catheter system 20 to be completely self-contained. It is believed that a completely self contained system would significantly reduce manufacturing costs by eliminating the need to manufacture separate equipment. Also, by negating the need for a separate inflation device, money may be saved with reduced inventory, reduced packaging requirements, reduced storage space requirements, and reduced medical waste. Furthermore, since the entire system may be prepped in one step and fewer connections are necessary, the reliability may be increased and the time required to prepare a catheter system for in-vivo use may be significantly reduced.

Figure 2:
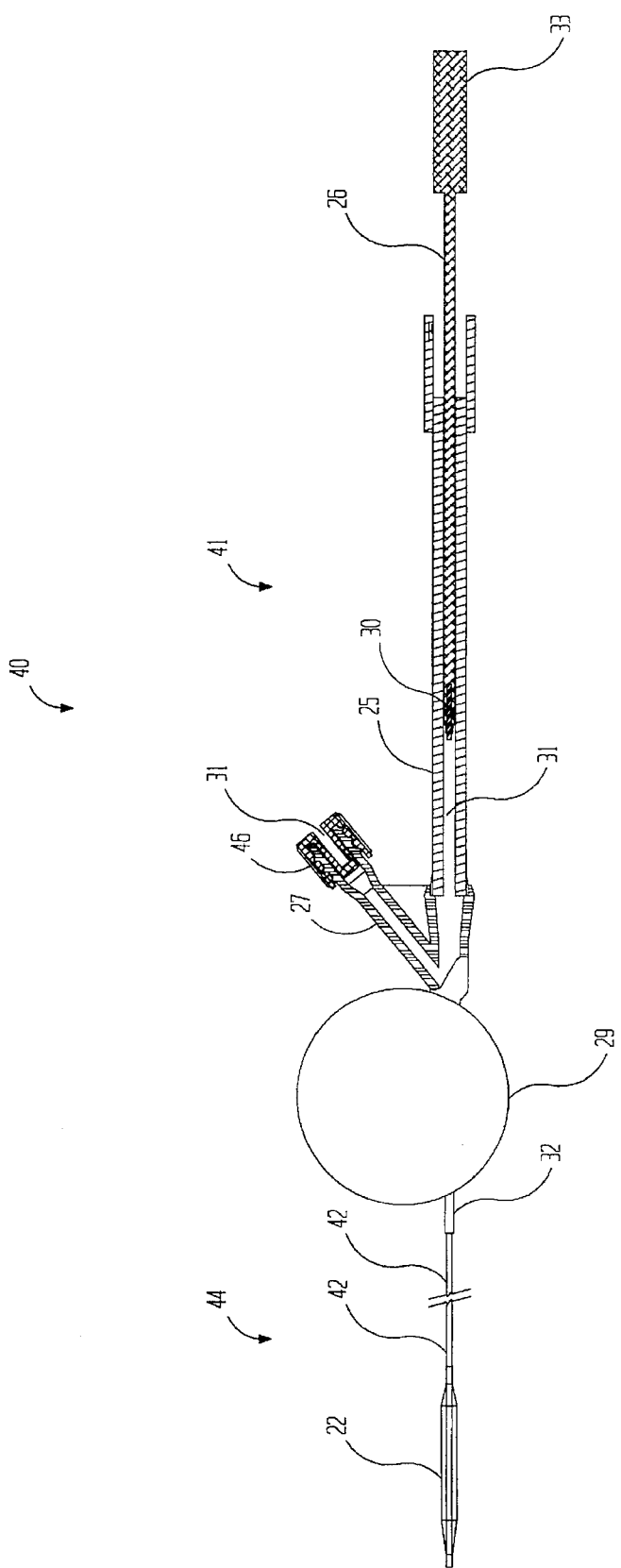
FIG. 2 is a partially sectioned view of a fixed-wire or single-operator-exchange type catheter system.

Refer now to the balloon catheter system 40 in FIG. 2 which is substantially identical to the balloon catheter system 20 in FIG. 1 with the following exceptions. FIG. 2 shows a FW or a SOE type balloon catheter 44 which differs from balloon catheter 43 in FIG. 1 only by the guide wire lumen design. The guide wire lumen 45 of OTW catheter 43 in FIG. 1 extends through the balloon 22, the elongate shaft 21 and the manifold 23. By contrast, FW type balloon catheters typically do not include a guide wire lumen in the conventional usage of the term. SOE type balloon catheters typically include a guide wire lumen which extends through only a distal portion of the shaft and the balloon. As such, typical FW and SOE type balloon catheters do not have a guide wire lumen extending through the manifold. Accordingly, the catheter system 40 does not show a guide wire lumen extending through the manifold 41.

As seen in FIG. 2, balloon catheter system 40 includes catheter 44 which may represent either a FW or SOE type balloon catheter 44 and has a manifold 41 connected to its proximal end. The FW/SOE type balloon catheter 44 may take on several forms which are known in the art. The FW/SOE balloon catheter 44 includes an elongate shaft 42 with a balloon 22 connected to its distal end. The proximal end of the elongate shaft 42 is connected to the manifold 41 by conventional means and utilizes a strain relief 32 to reduce the potential for kinking therebetween.

Manifold 41 is substantially identical to the manifold 23 as shown in FIG. 1 except that manifold 41 does not include a guide wire port and the associated elements. Manifold 41 includes a barrel 25 with a plunger 26 movably disposed therein. The plunger 26 includes a plunger seal 30 at its distal end and a handle 33 at its proximal end. The inside of the barrel 25 is in fluid communication with the inflation lumen 31 such that when the plunger 26 is longitudinally displaced, inflation fluid is displaced into or out of the inside of the barrel 25, through the inflation lumen 31 inside the shaft 42, and into or out of the balloon 22. As mentioned before, the construction of plunger 26, plunger seal 30, and barrel 25 are discussed in more detail with reference to FIG. 5.

Manifold 41 further includes a prep port 27 which may have a cap 46 or a stop-cock valve (not shown) releasably secured thereto. As with catheter system 20, the prep port 27 of catheter system 40 may be located on the proximal end of the catheter shaft 42, on the manifold 41 (shown), on the handle 33, or on any other portion of the catheter system 40 which has access to the inflation lumen 31 and does not interfere with in-vivo use. Manifold 41 also includes a generic pressure gauge 29 mounted thereon which is in fluid communication with the inflation lumen 31.

Figure 3:
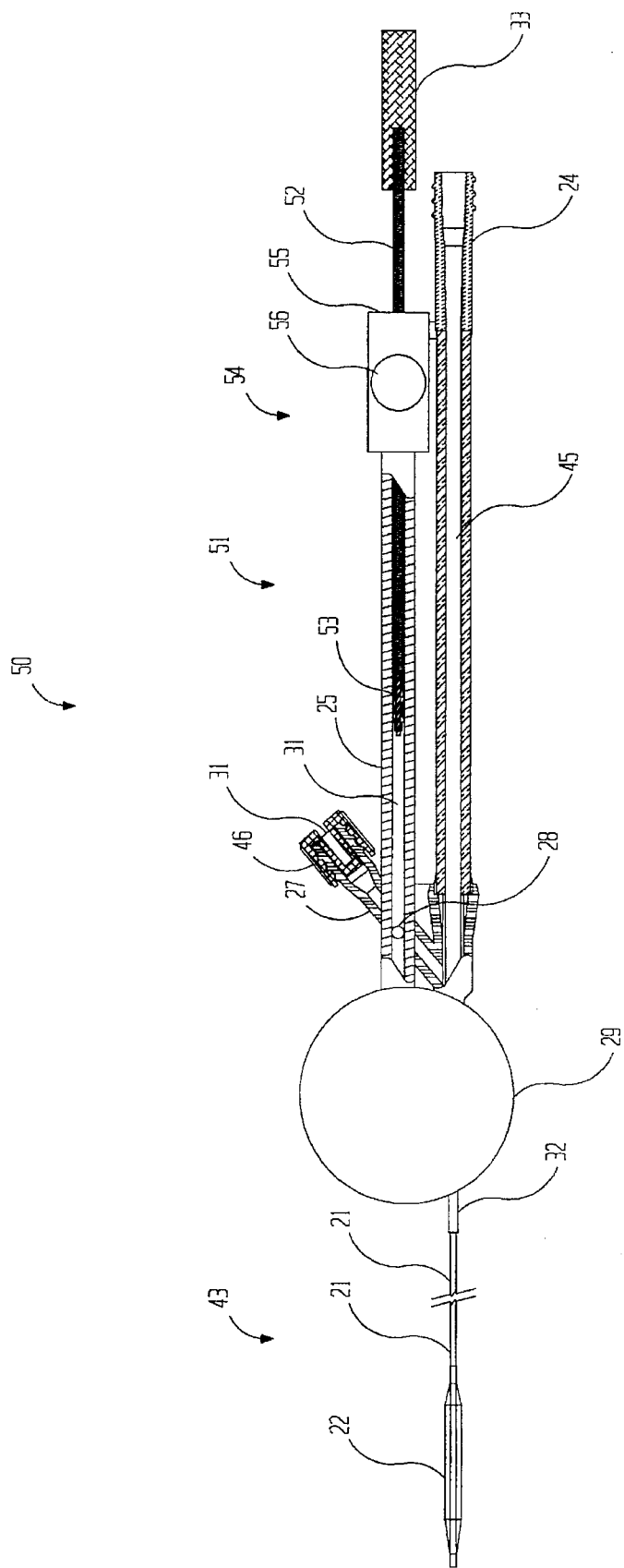

Refer now to the balloon catheter system 50 in FIG. 3 which is substantially identical to the balloon catheter system 20 in FIG. 1 with the exception of manifold 51. FIG. 3 shows manifold 51 which incorporates a different plunger 52 and plunger seal 53. Manifold 51 also incorporates a lock mechanism 54 attached to the barrel 25 which releasably locks onto plunger 52.

Threads on plunger 52 engage corresponding threads on lock mechanism 54 such that the plunger 52 may be displaced by rotating it relative to the lock mechanism 54. The thread count (threads per inch) on the plunger 52 and lock mechanism 54 allow the plunger 52 to be longitudinally displaced in small accurate increments. Since the inside diameter of the barrel 25 is relatively small as compared to a conventional 20 cc or 10 cc inflation device, incremental advancement of plunger 52 results in proportionately small volume displacement of inflation fluid and correspondingly small changes in balloon diameter. This allows the treating physician to gently and gradually inflate the balloon so that a vascular restriction may be dilated as atraumatically as possible. In addition, the threaded lock mechanism 54 allows the threaded plunger 52 to be advanced controllably to avoid over-inflation and dissection once the lesion yields. The construction of plunger 52 and plunger seal 53 is discussed in more detail with reference to FIG. 6.

Lock mechanism 54 includes push button 56 and housing 55 which contains the internal parts of the lock mechanism 54. Push button 56 is normally in the extended position from housing 55 by virtue of a biasing member located inside the housing 55. With the push button 56 in the extended position, the lock mechanism 54 engages the threads on the plunger 52 such that longitudinal displacement of the plunger 52 is only possible if the plunger 52 is rotated or the push button 56 is depressed to disengage the plunger (referred to as normally engaged). Although it is preferable to engage the plunger 52 in the normal position, it is also possible to be normally disengaged such that the plunger 52 is free to move unless the push button 56 is depressed. In the normally disengaged arrangement, depressing the push button 56 engages the threads on the plunger 52 such that the plunger 52 is only free to move longitudinally if the plunger 52 is rotated or if the push button 56 is released. For purposes of this discussion, the lock mechanism 54 is normally engaged but with a simple modification in the arrangement of the engaging parts, normally disengaged is also possible. The construction of lock mechanism 54 is discussed in more detail with reference to FIG. 8.

Figure 4:
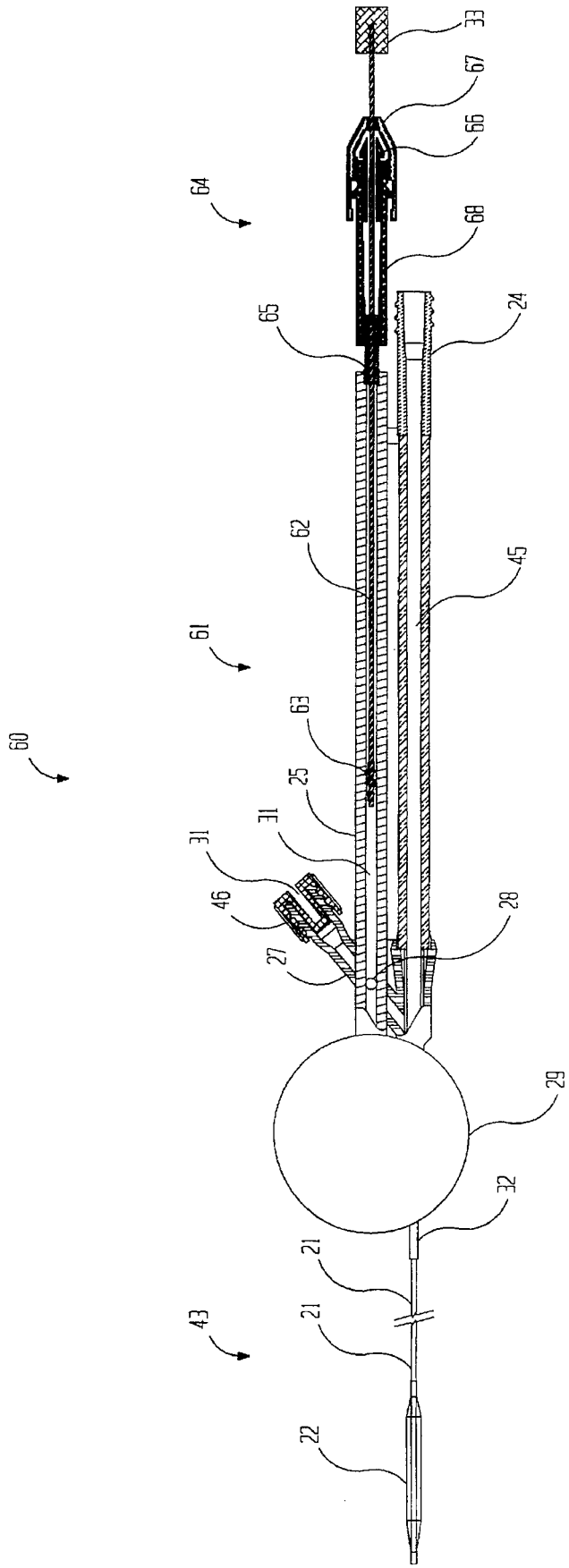

Refer now to the balloon catheter system 60 in FIG. 4 which is substantially identical to the balloon catheter system 20 in FIG. 1 with the following exceptions. Manifold 61 is similar to manifold 23 in FIG. 1 except that manifold 61 utilizes a different plunger 62 and plunger seal 63, and manifold 61 incorporates lock mechanism 64. The construction of plunger 62 and plunger seal 63 are discussed in more detail with reference to FIG. 7.

Continuing to refer to FIG. 4, lock mechanism 64 releasably secures plunger 62 such that plunger 62 may only be displaced when lock mechanism 64 is released. The lock mechanism 64 utilizes a collet 66 and a compression collar 67 similar to that of a conventional drill chuck or pin vise. Collet 66 rests inside retainer 68 and compression collar 67 screws onto retainer 68 securing the collet 66 therebetween. Retainer 68 is fixedly secured to barrel 25 by way of connection tube 65. This lock mechanism 64 allows the plunger 62 to be freely moved without the need to keep a release button depressed (as described with lock mechanism 54) thereby reducing the number of digital manipulations necessary to inflate and deflate the balloon.

It is contemplated that lock mechanism 64 may be used in place of lock mechanism 54 or used in combination. For example, if used in combination, connection tube 65 may include threads and extend further into barrel 25. The threaded connection tube would then pass through a lock mechanism similar to lock mechanism 54 which would allow for longitudinal movement of the connection tube only when rotated or disengaged. Thus, the plunger may be longitudinally displaced by rotation, by disengaging the threaded connection tube, or by disengaging the collet. The combination of lock mechanisms provides the treating physician the advantages of each without compromise.

Figure 5:
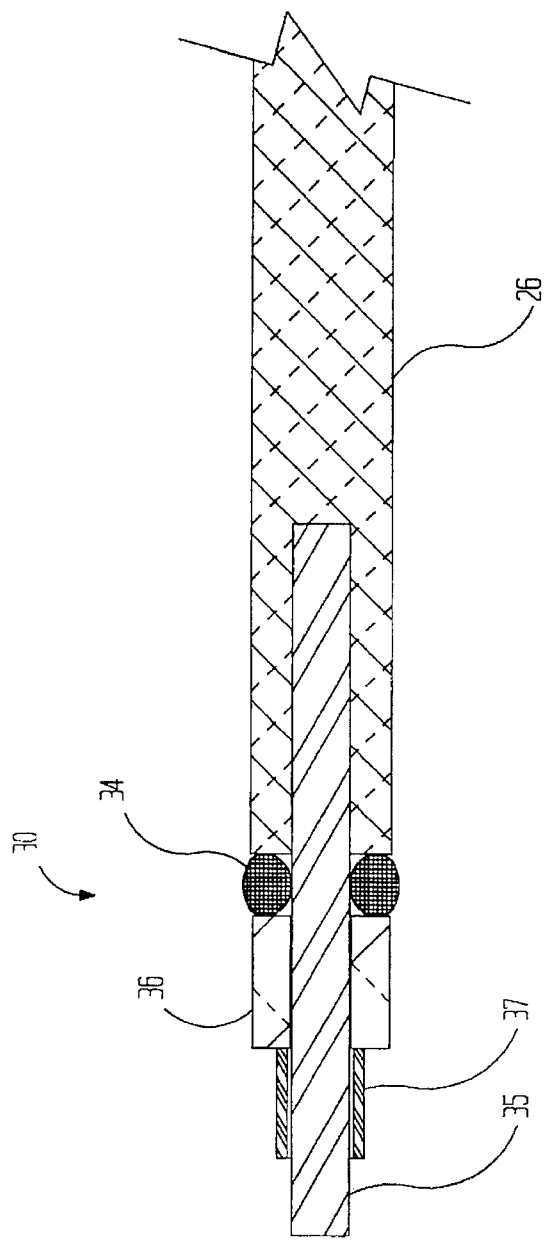
FIGS. 5, 6 and 7 are enlarged sectioned views of the plungers and plunger seals as shown in FIGS. 1, 3 and 4 respectively. The plunger and plunger seal designs are interchangeable consistent with the corresponding teachings for each figure.
Figure 6:
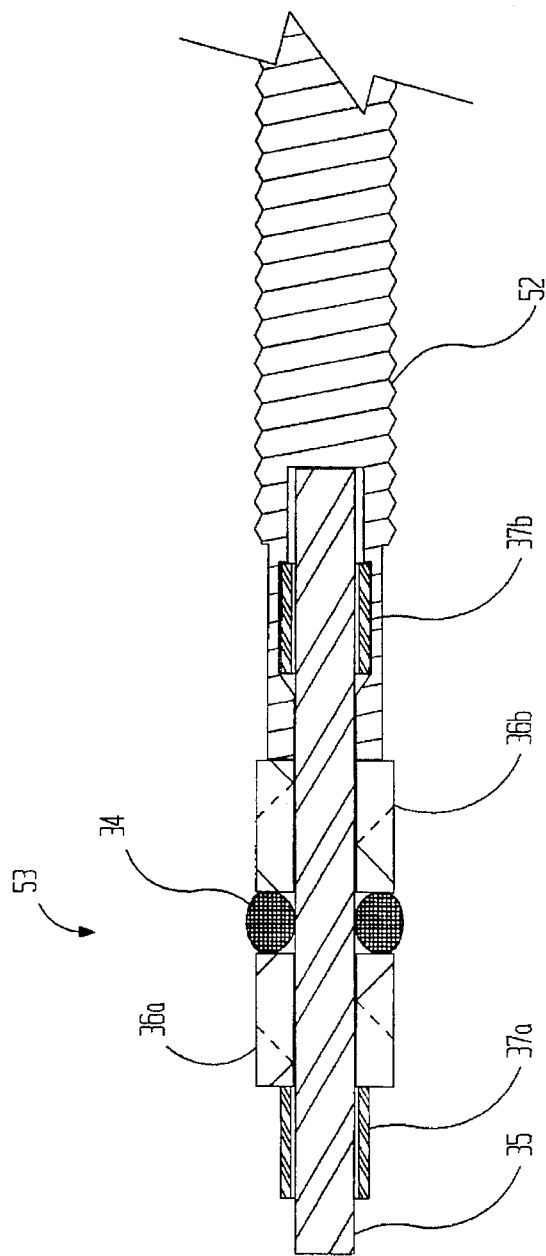
Figure 7:
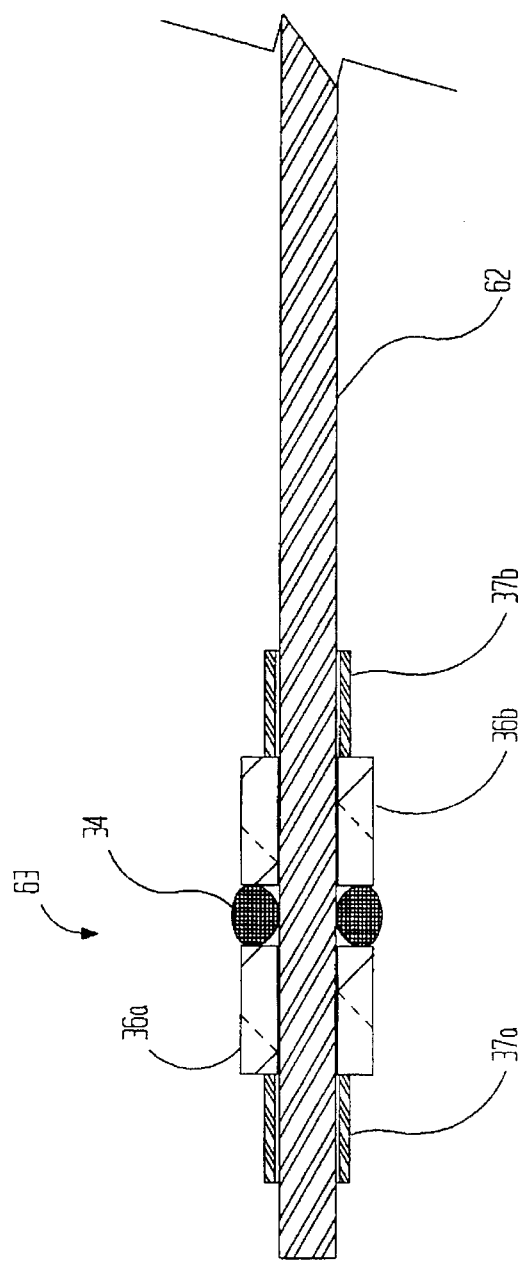

FIGS. 5–7 show several plunger and plunger seal designs which are interchangeable and may be modified to accommodate the particular lock mechanism used, if any. The barrel 25 construction for each different plunger is substantially the same. The length and inside diameter of the barrel 25 must be sufficient to allow for both proximal actuation to generate a vacuum in the balloon (i.e. deflate the balloon) and distal actuation to inflate the balloon to high pressures (e.g. 300 psi.). The internal volume of the barrel 25 is preferably minimized in order to minimize internal compliance, and the inside diameter is also preferably minimized in order to minimize the required actuation force. For example, if a conventional PTCA balloon (e.g. 20 mm length, 3.0 mm diameter) is used, a suitable length would be about 4 inches with an inside diameter of about 0.089 inches. The corresponding plunger would use an o-ring sized to provide a moving seal within the barrel. For example, the o-ring may have an outside diameter of 0.095 inches to seal inside a barrel with an inside diameter of 0.089 inches. Those skilled in the art would recognize that other seals could be used with the invention.

As stated previously, compliance may be reduced by providing a more rigid structure defining the fluid path and by decreasing the volume of inflation fluid and any air trapped in the fluid path. The volume of inflation fluid may be reduced by decreasing the volume of the fluid path. Accordingly, the small inside volume and the rigid structure of the barrel 25 significantly reduce the internal compliance. Low internal compliance is desirable because it increases the responsiveness of the system and eliminates the dampening effect on dynamic balloon response normally experienced with prior art catheters. In combination with the low friction movement of the plunger, the small inside volume and rigid structure of the barrel 25 allow the treating physician to better feel the response of the vascular restriction to the inflation of the balloon. In addition, low compliance reduces the tendency of the balloon to continue to expand after the lesion yields, thus reducing the probability of dissection. Furthermore, reduced internal compliance allows for a more rapid balloon inflation and deflation. Rapid balloon deflation allows the treating physician to more effectively relieve ischemia and other adverse reactions to prolonged balloon inflation. Rapid balloon inflation and deflation also allows for more effective use of the pulsating balloon technique. All together, the low internal compliance, low friction plunger, and small diameter barrel provide the treating physician with better and easier control of the dilation procedure.

The small inside diameter of the barrel 25 significantly reduces the force required to generate high inflation pressures, thereby reducing operator fatigue. The reduced actuation force allows one hand to hold the manifold and the thumb or finger(s) of the same hand to operate the plunger, thus only requiring a single operator. In addition, the small inside diameter of the barrel 25 correlates relatively large plunger displacement to relatively small changes in balloon diameter. Thus, the physician is able to feel slight changes in balloon diameter, perhaps caused by lesion recoil, by observing longitudinal displacement of the plunger. Also, since incremental advancement of plunger 52 results in proportionately small volume displacement of inflation fluid and correspondingly small changes in balloon diameter, the treating physician is able to gently and gradually inflate the balloon so that a vascular restriction may be dilated as atraumatically as possible. Once the lesion yields, the low compliance of the system maintains the balloon at substantially the same diameter thereby reducing the probability of dissection from over-dilation.

Note that the plunger displacement for a 0.089 inch inside diameter barrel from an empty balloon to a full balloon is approximately 36.6 mm for a 20 mm×3.0 mm PTCA balloon as compared to a conventional 20 cc inflation device (0.748 inch inside diameter barrel) which has a plunger displacement of only 0.518 mm. In addition, the plunger actuation force for a 0.089 inch barrel at 8 ATM is 0.731 lbs as compared to a conventional 20 cc inflation device (0.748 inch inside diameter barrel) which has an actuation force of 51.7 lbs.

FIG. 5 shows the plunger 26 used in the catheter systems of FIGS. 1 and 2. Plunger 26 may be made of polycarbonate with a diameter of 0.080 inches and a length of about 4 inches (excluding the handle 33). The handle 33 as best seen in FIG. 1 may also be made of polycarbonate and measures about 1.0 inches in length and 0.25 inches in diameter. Seal 30 includes an insert mandrel 35 which may be adhesively secured in a bore in the distal end of the plunger 26. The insert mandrel may be made of stainless steel and may measure 0.033 inches in diameter and about 0.4 inches in length. O-ring 34 may be made of Ethylene propylene rubber compound and measures 0.095 inches outside diameter by 0.029 inches inside diameter. The o-ring 34 is slid over insert 35 and is secured between the distal face of plunger 26 and retainer ring 36. Retainer ring 36 may be made of polycarbonate and measures 0.078 inches outside diameter by 0.035 inches inside diameter. Retainer ring 36 is kept in place on insert mandrel 35 by retainer ring 37. Retainer ring 37 may be made of stainless steel and measures 0.050 inches outside diameter by 0.038 inches inside diameter and may be secured to the insert mandrel by solder, braze or other weld. Other means to secure the o-ring may be utilized and must provide sufficient shear strength to resist fracture when the plunger 26 is longitudinally displaced to inflate or deflate the balloon.

FIG. 6 shows the plunger 52 used in catheter system 50 as seen in FIG. 3. Plunger 52 may be made of polycarbonate and measures about 4 inches in length with a major diameter of 0.080 inches and 56 threads per inch. Seal 53 includes insert mandrel 35 which fits into a bore in the distal end of the plunger 52 and is secured therein by a soldered retainer ring 37b made of stainless steel and measuring 0.050 inches outside diameter by 0.038 inches inside diameter. O-ring 34 is secured in place on insert mandrel 35 between polycarbonate retainers 36a and 36b measuring 0.078 inches outside diameter by 0.035 inches inside diameter. Retainer rings 36a and 36b are kept in place on insert mandrel 35 by retainer ring 37a and the distal face of plunger 52. Retainer ring 37a may be made of stainless steel and measures 0.050 inches outside diameter by 0.038 inches inside diameter and may be secured to the insert mandrel by solder, braze or other weld. As mentioned before, other means to secure the o-ring 34 may be utilized and must provide sufficient shear strength to resist fracture when the plunger 26 is longitudinally displaced to inflate or deflate the balloon.

FIG. 7 shows plunger 62 and plunger seal 63 as used with catheter system 60 in FIG. 4. Plunger 62 may be made of stainless steel and measures about 4 inches in length with a diameter of about 0.033 inches. O-ring 34 is secured in place on plunger 62 between polycarbonate retainers 36a and 36b measuring 0.078 inches outside diameter by 0.035 inches inside diameter. Retainer rings 36a and 36b are kept in place on insert mandrel 35 by retainer rings 37a and 37b. Retainer rings 37a and 37b may be made of stainless steel and measure 0.050 inches outside diameter by 0.038 inches inside diameter and may be secured to the plunger 62 by solder, braze or other weld. Again, other means to secure the o-ring 34 may be utilized and must provide sufficient shear strength to resist fracture when the plunger 26 is longitudinally displaced to inflate or deflate the balloon.

Figure 8:
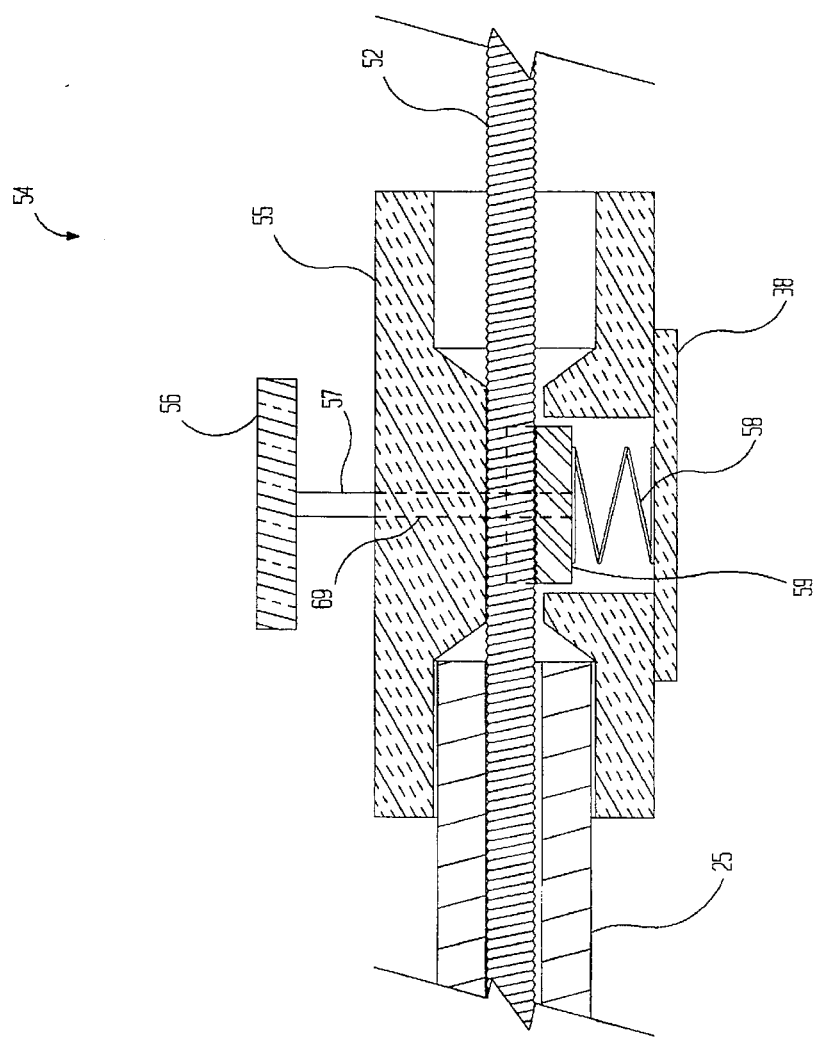
FIG. 8 is an enlarged sectioned view of the lock mechanism as shown in FIG. 3.

FIG. 8 shows the lock mechanism 54 as used with catheter system 50 in FIG. 3. Lock mechanism 54 includes housing 55 made of polycarbonate and rigidly connected to the proximal end of the barrel 25. Plunger 52 passes through housing 55 and into the barrel 25. As discussed in more detail with reference to FIG. 6, plunger 52 includes threads which match to engage the threads on nut 59. Nut 59 may be made of nylon and may be disengaged from plunger 52 by depressing button 56. Button 56 may be made of nylon and is slidably disposed in housing 55. Nut 59 is connected to button 56 by way of a pair of rods 69 straddling the plunger 52. The pair of rods 69 are connected to button rod 57 which is connected to button 56. Rods 57, 69 may be made of nylon with connections made by a suitable adhesive or weld joint. Nut 59 normally engages plunger 52 due to biasing member 58 which, for example, may be a conventional spring. The nut 59 may be placed on the opposite side of plunger 52 to create a normally disengaged arrangement. Biasing member 58 is secured within housing 55 by spring plate 38 made of polycarbonate and adhesively secured to housing 55.

Figure 9:
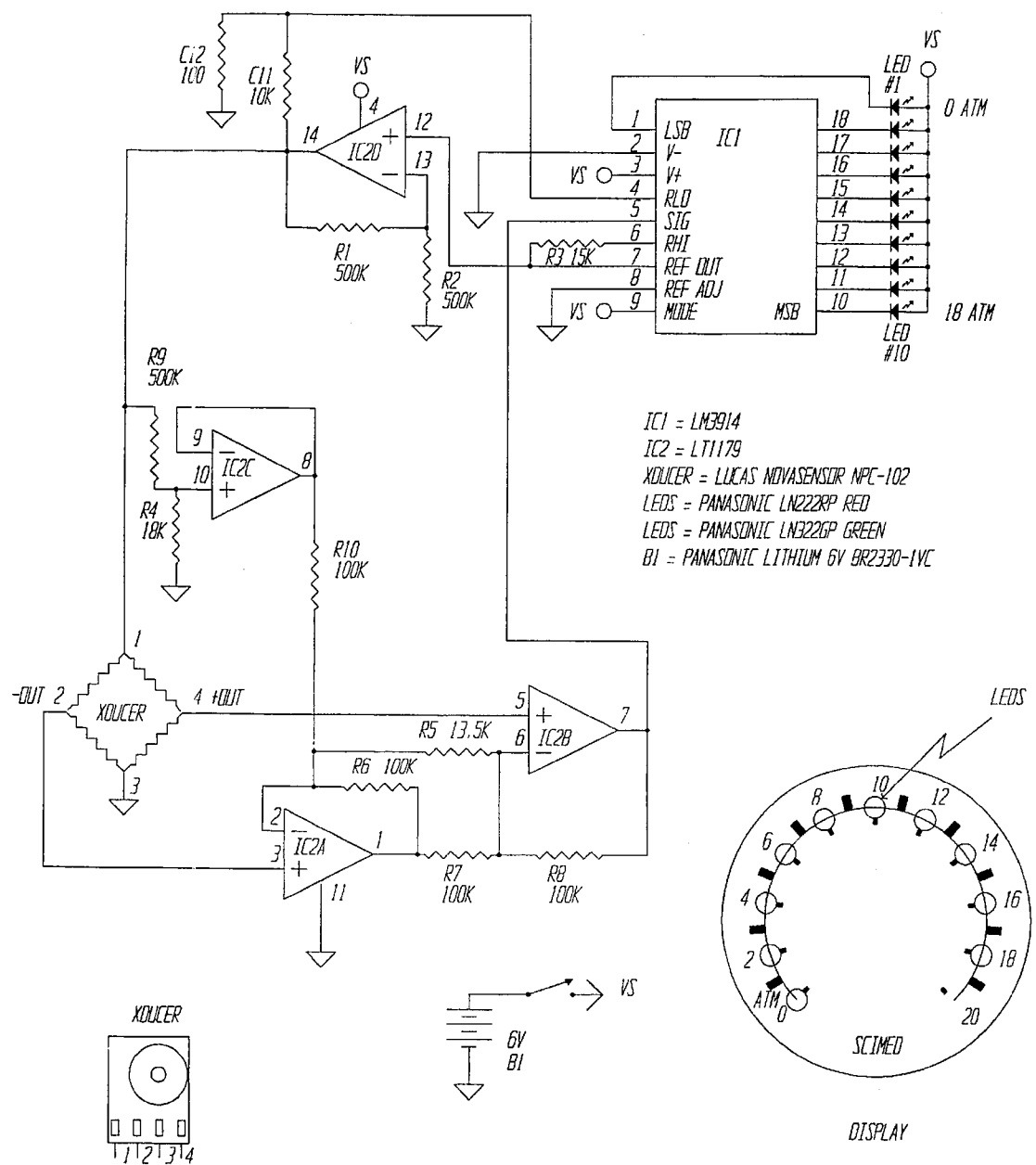
FIG. 9 is a schematic diagram of a circuit for use with an electronic analog pressure display.

FIG. 9 shows a schematic diagram of circuit for an electronic analog type pressure gauge which is particularly suitable for use with the present invention. The electronic analog gauge provides a low compliance, highly responsive means to monitor dynamic pressure, such as an oscillating pressure. The analog feature allows rapid changes in pressure to be observed which would otherwise not be observable with a digital gauge. FIG. 9 also shows an example of a display (labeled DISPLAY) for the analog gauge and a diagram of a suitable pressure transducer (labeled XDUCER). The circuit diagram shows the appropriate connections of the components and also lists the value or descriptor for each component. All resistors may be one tenth watt or larger. The LEDs may be arranged on the display with green LED #1 representing zero pressure or vacuum and red LEDs #2–10 representing 2 ATM–18 ATM respectively. A suitable pressure transducer is model number NPC-102 available from Nova Sensor. Integrated circuit IC1 serves to provide a linear analog display with discrete LEDs. Integrated circuits IC2A, B, C and D serve to provide reference voltage bias to the sensor and differential amplification of the sensor output.

In practice, the present invention may be used in the following manner. Prior to in-vivo use, all the gas inside the inflation lumen, the balloon and the barrel must be replaced with a liquid such as radiopaque contrast saline solution. This may be done by connecting a fluid source, such as a 20 cc syringe or other vacuum source containing the liquid solution, to the prep port. The gas is then displaced using conventional negative prep methods. Prior to displacing the gas with liquid, the plunger is placed in a neutral position such that it may be longitudinally moved both distally and proximally to inflate and deflate the balloon. The fluid source is then disconnected from the prep port and the prep port is closed with a cap or other seal means. The balloon catheter may then be placed in-vivo and the balloon inflated by displacing the plunger distally to urge inflation fluid out of the barrel and into the balloon by way of the inflation lumen. The balloon may be deflated by displacing the plunger proximally to draw the inflation fluid back into the barrel. The steps of inflating and deflating may be repeated as necessary. In addition, balloon inflation and deflation may be repeated in rapid succession to essentially oscillate the diameter of the balloon.

It is contemplated that the volume of a lesion, the physical characteristics of a lesion, and lesion elastic recoil may be detected utilizing the present invention. This is possible because of the low compliance of the present invention and the low friction, small bore barrel and plunger. Balloon volume (i.e. the volume of inflation fluid in the balloon) is directly and inversely related to lesion volume. Balloon volume, in turn, is proportional to plunger displacement which is easily measured by several methods. For example, plunger displacement may be measured with a linear transducer (e.g. Lucas Scheevitz model 250 DCE linear transducer) connected to the plunger or with a series of incremental marks on the plunger or the (transparent) barrel. Thus, lesion volume may determined by measuring plunger displacement. Because the present invention utilizes a small bore barrel and plunger, lesion volume may be accurately determined.

In a similar manner, the physical characteristics of a given lesion may be determined. This may be accomplished by comparing the change in volume of the lesion (as measured by plunger displacement) to the force (as measured by plunger actuation force) required to change the lesion volume. Because of the low compliance of the present invention, the lesion volume may be accurately determined at both lower and higher inflation pressures. The actuation force of the plunger may be measured at various plunger positions and a force versus volume plot may be generated. Alternatively, the treating physician may take mental notes of the resistance to plunger displacement versus the position of the plunger to feel the physical characteristics of the lesion. Thus, the treating physician obtains valuable information about the physical characteristics of the lesion and is better able to predict the results of balloon dilatation.

Elastic lesion recoil (also referred to as abrupt reclosure) after balloon dilatation may be detected in a similar manner. Elastic recoil refers to the response of a lesion to balloon dilation wherein the lesion returns to its original undilated state. Elastic recoil is difficult to predict and can have devastating clinical effects. The present invention provides a method of detecting elastic recoil and avoiding clinical complications. Due to the low friction, small bore barrel and plunger of the present invention, changes in lesion volume are easily detectable as described previously. In particular, when the lesion recoils, inflation fluid in displaced from the balloon and into the barrel, thus longitudinally displacing the plunger. Although only a small volume of fluid may be displaced, the low friction, small bore barrel correlates small changes in volume into easily detectable plunger displacement. Thus, the treating physician may dilate a lesion, release the plunger, and wait to see if the lesion recoils. In doing so, the treating physician avoids potential clinical complications, retains access to the lesion, and may change the therapy as needed (e.g. utilize a stent).

An alternative method is contemplated which utilizes an impact on the plunger to generate a pressure spike within the balloon. For example, a hammer or other impact generating instrument may be used to strike the plunger. The impact of such a strike has been shown to produce a 18-20 ATM pressure for about 2-5 milliseconds inside the barrel. The pressure spike sends pressure waves to the balloon in the range of 12-15 ATM for about 2-5 milliseconds. Possible clinical benefits may result from rapid stress—strain created by hammering. For example, resistant lesions (e.g. highly calcified lesions) may yield to the rapid stress—strain dilation but not conventional dilation. Also, the rapid stress—strain may be used to better deform and tack metal stents, potentially improving the final stented lumen.

FIGS. 10-13 show the balloon response of the present invention to various conditions. The balloon catheter system used was substantially similar to the system depicted in FIG. 1 and included a SCIMED NC Cobra™ 14—3.0 mm×20 mm balloon catheter. The balloon response was measured by positioning the balloon in a fixture including a Lucas Scheevitz model 250 DCE linear transducer electrically connected to a TEK 2232 oscilloscope. The linear transducer was positioned to abut one side of the balloon and a stop plate was positioned to abut the other side of the balloon. With this arrangement, changes in balloon diameter caused displacement of the linear transducer as recorded by the oscilloscope. The pressure inside the barrel was measured by a Lucas Nova model NPC-102 pressure sensor electrically connected to the TEK 2232 oscilloscope by way of a Frequency Devices model 9002 filter instrument.

Figure 10:
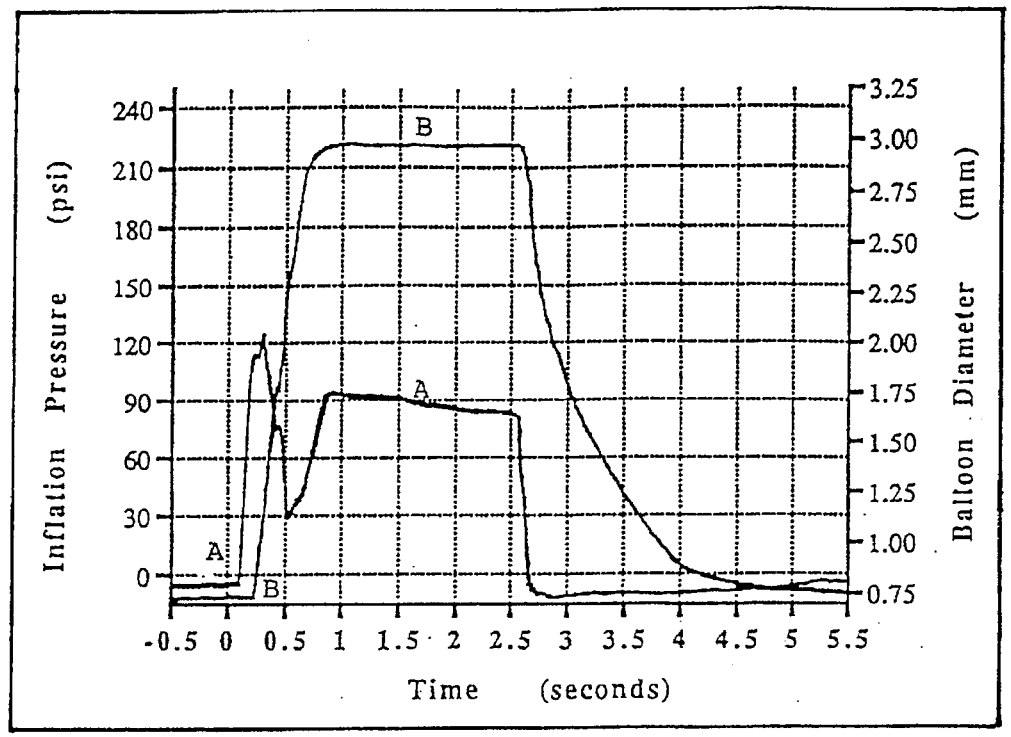
FIGS. 10–12 show the response of the present invention to various conditions. In particular.

FIG. 10 shows the balloon response of the present invention to a single inflation and deflation. The balloon was inflated by manually pushing the plunger and holding it at a specified pressure. The pressure curve is denoted by the letter A and the balloon response curve is denoted by the letter B. The balloon response graph of FIG. 10 demonstrates the increased responsiveness of the present invention. The tested specimen had a inflation time lag of approximately 0.2 seconds from initial inflation pressure to balloon response and a deflation time lag of approximately 2.0 seconds from initial deflation pressure to full balloon deflation.

Figure 11:
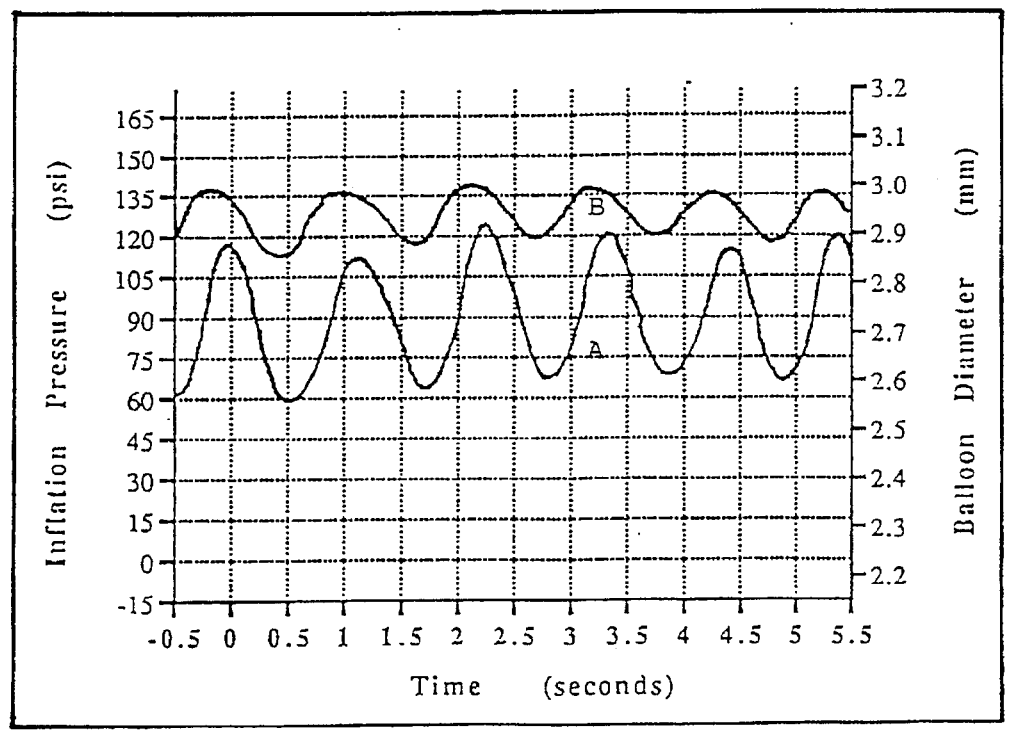

FIG. 11 shows the balloon response to cyclic inflation and deflation. Cyclic inflation and deflation may be accomplished by manually actuating the plunger with the finger or hand, or by automatically actuating the plunger with a solenoid or similar oscillating mechanism. The same test arrangement and test specimen as discussed with reference to FIG. 10 was used for the test corresponding to FIG. 11, and the plunger was manually oscillated. The pressure curve is denoted by the letter A and the balloon response curve is denoted by the letter B. The balloon response graph of FIG. 11 demonstrates the increased responsiveness of the present invention and in particular the benefits of reduced internal compliance as compared to a conventional inflation device and catheter system. The present invention has a noticeably responsive balloon with a diameter varying from about 2.85 mm to about 3.0 mm at a matching frequency of 1.0 Hz to the oscillating inflation pressure with an amplitude of approximately 4-8 ATM at a frequency of about 1.0 Hz. Thus, the internal compliance of the present invention is sufficiently low to permit effective balloon response to cyclic inflation pressure, whereas the compliance of prior art systems are sufficiently high to dampen the effect of the cyclic inflation. This feature may be of particular significance when the pulsating balloon technique is used to atraumatically dilate difficult lesions at low pressure. Some physicians strongly believe that lesions subjected to pulsating inflation may yield at a lower average pressure and cause fewer dissections of the artery resulting in overall better patient outcome.

Figure 12:
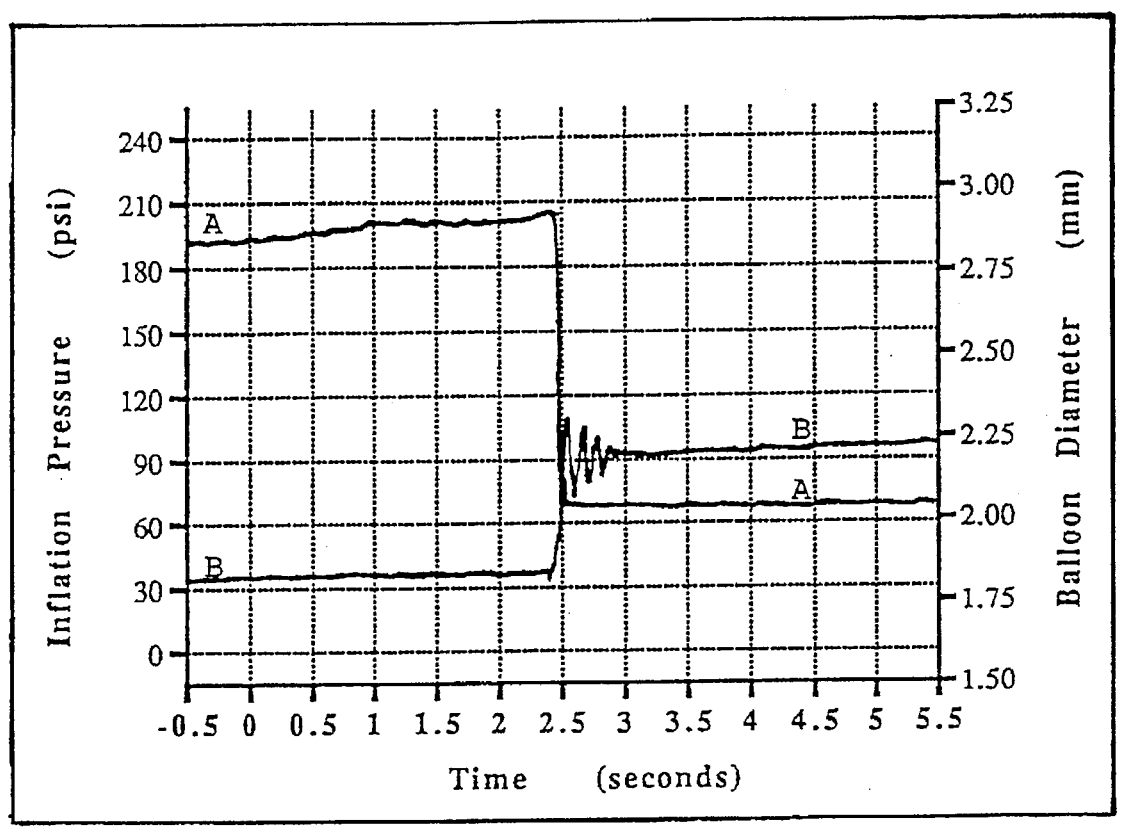

Now refer to FIG. 12 which demonstrates the response of a synthetic arterial lesion to balloon dilation. The same test apparatus as described with reference to FIG. 10 is used in this experiment except that a synthetic calcium carbonate annular lesion is placed around the balloon. As shown in FIG. 12, the inflation pressure (curve labeled A) is gradually increased to about 13.6 ATM with a corresponding balloon diameter of about 1.8 mm when the synthetic lesion cracks (curve labeled B). When the lesion cracks, the balloon pressure instantly drops to about 4.7 ATM and the balloon diameter increases only slightly to about 2.2 mm. Thus, the relatively low internal compliance allows the balloon to be inflated to high pressures without causing over-dilation as could occur with a conventional inflation device having higher internal compliance. The significantly reduced compliance of the present invention reduces the potential for dissection or crack propagation after the lesion is cracked thereby increasing the potential for favorable clinical results.

While the specification describes the preferred constructions, materials, dimensions, methods of manufacture and methods of practice, those skilled in the art will appreciate the scope and spirit of the invention with reference to the appended claims.

What is claimed is:

1. A balloon catheter insertable into a living body, comprising:
   (a) an elongate shaft having a proximal end, a distal end and an inflation lumen extending therethrough;
   (b) an inflatable balloon connected to the distal end of the shaft and in fluid communication with the inflation lumen;
   (c) a manifold connected to the proximal end of the shaft, the manifold having a barrel containing a plunger movably disposed therein, the barrel being in fluid communication with the inflation lumen, the barrel having an internal volume less than 5 cc and an internal diameter of less than 0.25 inches; and
   (d) a prep port connected to the catheter and being in fluid communication with the inflation lumen, the prep port being releasably connectable to a fluid source.

2. A balloon catheter as in claim 1 wherein the manifold is sized to be held in one hand and the plunger is positioned and sized to be actuated by a thumb or finger on the one hand.

3. A balloon catheter as in claim 2 wherein the manifold is sized to be held in one hand and the plunger is positioned and sized to be actuated by a thumb or finger on the one hand.

4. A balloon catheter as in claim 3, further including:
   (e) a seal connected to the prep port for sealing the inflation lumen from the exterior of the catheter.

5. A balloon catheter as in claim 4 wherein the seal is a removable cap.

6. A balloon catheter as in claim 4 wherein the seal is a valve.

7. A balloon catheter as in claim 4, further including:
   (f) a pressure transducer mounted on the catheter and being in fluid communication with the inflation lumen to measure pressure therein.

8. A balloon catheter as in claim 7, further including:
   (g) a pressure display operably connected to the pressure transducer.

9. A balloon catheter as in claim 8 wherein the pressure display is connected to the catheter.

10. A balloon catheter as in claim 8 wherein the pressure display is remotely located from the catheter.

11. A balloon catheter as in claim 10 wherein the pressure transducer communicates with the display by electrical wire.

12. A balloon catheter as in claim 10 wherein the pressure transducer communicates with the display by wireless transmission.

13. A balloon catheter as in claim 12 wherein the wireless transmission is an infrared transmission.

14. A balloon catheter as in claim 12 wherein the wireless transmission is a radio frequency transmission.

15. A balloon catheter as in claim 12 wherein the wireless transmission is a magnetic transmission.

16. A balloon catheter as in claim 7 wherein the display is digital.

17. A balloon catheter as in claim 7 wherein the display is analog.

18. A balloon catheter as in claim 7 wherein the display is digital and analog.

19. A balloon catheter as in claim 7 wherein the display displays pressure.

20. A balloon catheter as in claim 7 wherein the display displays time.

21. A balloon catheter as in claim 19 wherein the pressure display is analog.

22. A balloon catheter as in claim 20 wherein the time display is digital.

23. A balloon catheter as in claim 3 further including:
   (e) a lock mechanism connected to the barrel.

24. A balloon catheter as in claim 3 further including:
   (e) a displacement indicator disposed on the manifold to indicate the longitudinal displacement of the plunger relative to the barrel.

25. A balloon catheter system, comprising:
   (a) a balloon catheter, the balloon catheter including;
      (i) an elongate shaft having a proximal end, a distal end and an inflation lumen extending therethrough;
      (ii) an inflatable balloon connected to the distal end of the shaft and in fluid communication with the inflation lumen; and
      (iii) a manifold connected to the proximal end of the shaft, the manifold having an inflation port, the inflation port being in fluid communication with the inflation lumen;
   (b) and an inflation device connected to the inflation port, the inflation device including;
      (i) a barrel in fluid communication with the inflation lumen, the barrel having an internal volume less than 5 cc and an internal diameter of less than 0.25 inches;
      (ii) a plunger movably disposed in the barrel; and
      (iii) a connection port disposed on the inflation device for connection to the manifold on the catheter.

26. A balloon catheter system as in claim 25 wherein the inflation device is fixedly connected to the inflation port.

27. A balloon catheter system as in claim 25 wherein the inflation device is releasably connected to the inflation port.

28. A balloon catheter system as in claim 25, wherein the inflation device further includes:
   (iv) a prep port disposed on the inflation device, the prep port being in fluid communication with the inflation lumen of the catheter when the connection port is connected to the manifold of the catheter.

29. A balloon catheter system as in claim 25, further including:
   (d) a pressure transducer mounted on the catheter and being in fluid communication with the inflation lumen to measure pressure therein.

30. A balloon catheter system as in claim 29, further including:
   (e) a pressure display operably connected to the pressure transducer.

31. A balloon catheter as in claim 30, further including:
   (f) a timer display attached to the pressure display.

32. A balloon catheter system as in claim 30 wherein the pressure display is an electronic analog display.

33. A balloon catheter system as in claim 31 wherein the pressure display is an electronic analog display and the timer display is an electronic digital display.

34. A balloon catheter system as in claim 30 wherein the seal is a removable cap.

35. A balloon catheter system as in claim 30 wherein the seal is a valve.

36. A balloon catheter system as in claim 25, further including: (c) a first lock mechanism connected to the barrel.

37. A balloon catheter system as in claim 36 wherein the first lock mechanism includes a biasing member which causes the first lock mechanism to normally engage the plunger.

38. A balloon catheter system as in claim 36 wherein the first lock mechanism includes a threaded portion, the plunger includes a threaded portion, and the threaded portion on the first lock mechanism engages the threaded portion on the plunger such that the plunger may be longitudinally fixed relative to the first lock mechanism or may be longitudinally displaced relative to the first lock mechanism by rotating the plunger or disengaging the threaded portions.

39. A balloon catheter as in claim 36 wherein the first lock mechanism includes a collet which releasably engages the plunger such that the plunger may be longitudinally fixed relative to the first lock mechanism or may be longitudinally displaced relative to the first lock mechanism by disengaging the collet.

40. A balloon catheter system as in claim 36, further including:

(d) a second lock mechanism connected to the plunger.

41. A balloon catheter system as in claim 40 wherein the first lock mechanism includes a threaded portion, the plunger includes a threaded portion, the threaded portion on the first lock mechanism engages the threaded portion on the plunger such that the plunger may be longitudinally fixed relative to the first lock mechanism or may be longitudinally displaced relative to the first lock mechanism by rotating the plunger or disengaging the threaded portions; and the second lock mechanism includes a collet which releasably engages the plunger such that the plunger may be longitudinally fixed relative to the second lock mechanism or may be longitudinally displaced relative to the second lock mechanism by disengaging the collet.

42. A balloon catheter system as in claim 28, further including:

(c) a seal connected to the prep port for sealing the inflation device during balloon inflation.

* * * * *